US012714348B2

(12) United States Patent
Purdon et al.

(10) Patent No.: US 12,714,348 B2
(45) Date of Patent: Aug. 25, 2026

(54) UNIVERSAL EEG CAP WITH CARBON FIBER-BASED CONDUCTIVE SILICONE SPONGE ELECTRODES AND FABRIC-PRINTED ELECTRODE-CONNECTING WIRES

(71) Applicants: Steven Purdon, Montgomery, TX (US); Caitlin Byrd, Burnet, TX (US); Jeffrey Whaley, Cumming, GA (US)

(72) Inventors: Steven Purdon, Montgomery, TX (US); Caitlin Byrd, Burnet, TX (US); Jeffrey Whaley, Cumming, GA (US)

( * ) Notice: Subject to any disclaimer, the term of this patent is extended or adjusted under 35 U.S.C. 154(b) by 0 days.

(21) Appl. No.: 18/862,047

(22) PCT Filed: May 24, 2023

(86) PCT No.: PCT/US2023/023364
§ 371 (c)(1),
(2) Date: Oct. 31, 2024

(87) PCT Pub. No.: WO2023/230133
PCT Pub. Date: Nov. 30, 2023

(65) Prior Publication Data

US 2025/0255531 A1 Aug. 14, 2025

Related U.S. Application Data

(60) Provisional application No. 63/345,088, filed on May 24, 2022.

(51) Int. Cl.

| | |
|---|---|
| ***A61B 5/291*** | (2021.01) |
| ***A61B 5/00*** | (2006.01) |

(Continued)

(52) U.S. Cl.
CPC .............. *A61B 5/291* (2021.01); *A61B 5/256* (2021.01); *A61B 5/268* (2021.01); *A61B 5/6803* (2013.01);
(Continued)

(58) Field of Classification Search
None
See application file for complete search history.

(56) References Cited

U.S. PATENT DOCUMENTS 8,916,262 B2 12/2014 Hook et al.
9,962,313 B2 5/2018 Scott et al.
(Continued)

FOREIGN PATENT DOCUMENTS

WO 2020010219 A1 1/2020

OTHER PUBLICATIONS

Vasios, Christos, et al., EEG/(f)MRI measurements at 7 Tesla using a new EEG cap ("InkCap"), 2006, Elsevier, NeuroImage 33, pp. 1082-1092 (Year: 2006).*
(Continued)

*Primary Examiner* — Aurelie H Tu
(74) *Attorney, Agent, or Firm* — Buchalter LLP

(57) ABSTRACT

An improved electroencephalogram (EEG) cap. In one embodiment, the EEG cap comprises a head covering comprising auxetic fabric, wherein the auxetic fabric allows the head covering to fit on and conform to a head, wherein the head is any shape and size; one or more electrodes disposed on an internal surface of the head covering, wherein each of the one or more electrodes comprise a conductive sponge comprising a two-part silicone foam, a silicone thinning fluid, and carbon fiber, and a sponge seat comprising a silicone or thermoplastic elastomer material, wherein the conductive sponge is disposed within the sponge seat; and one or more wires printedly embedded in the head covering (Continued)

that connect the one or more electrodes to external electronics.

27 Claims, 5 Drawing Sheets

(51) Int. Cl.
*A61B 5/256* (2021.01)
*A61B 5/268* (2021.01)

(52) U.S. Cl.
CPC . *A61B 2560/0468* (2013.01); *A61B 2562/046* (2013.01); *A61B 2562/164* (2013.01); *A61B 2562/227* (2013.01)

(56) References Cited

U.S. PATENT DOCUMENTS

| | | | | |
|---|---|---|---|---|
| 11,311,220 | B1 | 4/2022 | Moinuddin et al. | |
| 2001/0044573 | A1* | 11/2001 | Manoli | A61B 5/6804 600/383 |
| 2003/0032888 | A1* | 2/2003 | Dewan | G06F 3/015 600/545 |
| 2016/0022165 | A1 | 1/2016 | Sackellares et al. | |
| 2019/0015238 | A1 | 1/2019 | Mottram et al. | |
| 2021/0122895 | A1 | 4/2021 | Krishnan et al. | |
| 2021/0393955 | A1 | 12/2021 | Hagedorn | |

OTHER PUBLICATIONS

PCT Notification Concerning Transmittal of International Preliminary Report on Patentability for Application No. PCT/US23/23364 dated Dec. 5, 2024.

PCT International Search Report and Written Opinion for Application No. PCT/US23/23364 dated Dec. 7, 2023.

* cited by examiner 200
250
100
20
1
40
45
20
2
3
20
20
20
280
7
6
20
210
4
260
5
210
20
290
8
20
20
20
9
20
270

39

20
25
27
26
24

28
29
20
25
24
27
32
26

25
A
32
24
28
A
26

39
B
28
28
25
SECTION A-A

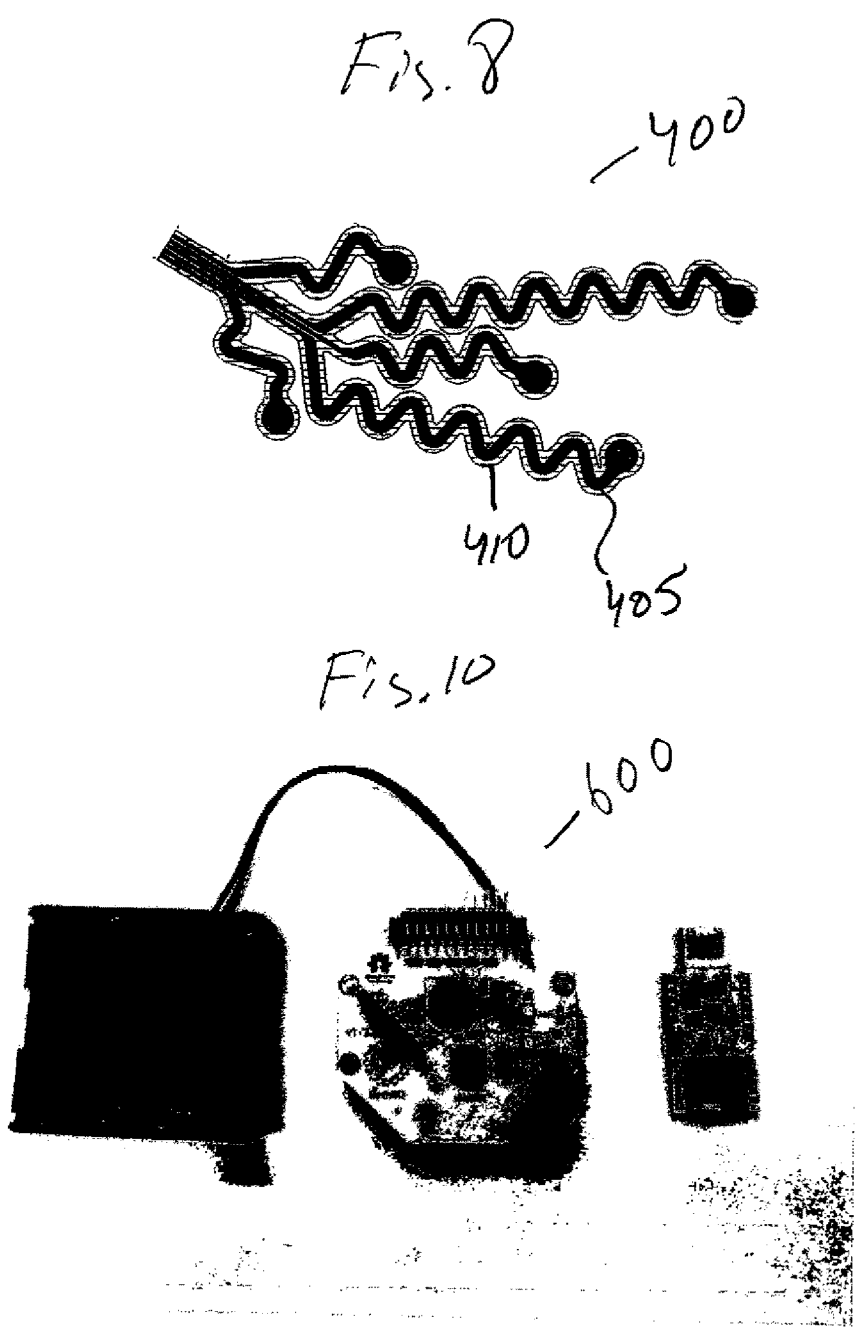
Fig. 8
400
410
405
Fig. 10
600
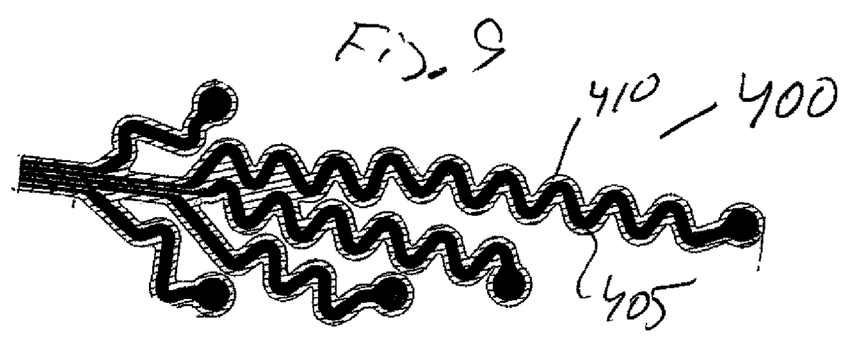
Fig. 9
410
400
405

UNIVERSAL EEG CAP WITH CARBON FIBER-BASED CONDUCTIVE SILICONE SPONGE ELECTRODES AND FABRIC-PRINTED ELECTRODE-CONNECTING WIRES

CROSS-REFERENCE TO RELATED APPLICATIONS

This application is a non-provisional application that claims the benefit of U.S. Application Ser. No. 63/345,088 filed May 24, 2022, the disclosure of which is incorporated by reference herein in its entirety.

STATEMENT REGARDING FEDERALLY SPONSORED RESEARCH OR DEVELOPMENT

Not applicable.

BACKGROUND OF THE INVENTION

Field of the Invention

The present invention relates to the field of electroencephalography and electroencephalograms (EEGs). More particularly, the present invention relates to an improved, universally fitting EEG cap comprising carbon fiber-based conductive silicone sponge electrodes and fabric-printed electrode-connecting wires.

Background of the Invention

Electroencephalography is a non-invasive method of measuring a brain's electrical activity via an EEG that may be widely used in epilepsy diagnosis, studying neurological disorders, neuroscientific studies, and brain-machine interfaces. Typically, an EEG utilizes various equipment such as electrodes, connecting wires, amplifiers, a computer control module, and a display device to offer high temporal resolution during testing, however such equipment may often be limited to low spatial resolution during testing due to low-electrode counts. To mitigate this shortcoming, high-density EEG (HD-EEG) systems have been developed which incorporate the use of several hundred electrodes. While these HD-EEG systems have potential to become low-cost imaging technology that improves spatial resolution, their developments may have some challenges.

For instance, to correctly localize an epileptic seizure, there may be a need to measure EEG signals before and at the onset of a seizure, requiring extended-time HD-EEG recordings. As such, HD-EEG equipment setup time, setup ease, type, and longevity may be highly important considerations. Currently, HD-EEG equipment may utilize EEG caps that incorporate electrodes and connecting wires to thereby improve setup time and ease. However, such EEG caps may require manufacturing in various sizes to accommodate users of variously sized heads, and further may utilize electrodes known in the art that have various shortcomings. For example, current EEG caps may utilize wet electrodes, that while capable of providing a high Signal-to-Noise Ratio (SNR), may be cumbersome to setup. Alternatively, current EEG caps may utilize dry electrodes, that while less cumbersome to setup, may provide a poor SNR.

Consequently, there is a need for an improved, universally fitting EEG cap that incorporates high performing electrodes and electrode-connecting wires. More particularly, there is a need for an improved, universally fitting EEG cap comprising carbon fiber-based conductive silicone sponge electrodes and fabric-printed electrode-connecting wires.

BRIEF SUMMARY OF SOME OF THE PREFERRED EMBODIMENTS

These and other needs in the art are addressed in one embodiment by an electroencephalogram (EEG) cap, comprising a head covering comprising auxetic fabric, wherein the auxetic fabric allows the head covering to fit on and conform to a head, wherein the head is any shape and size; one or more electrodes disposed on an internal surface of the head covering, wherein each of the one or more electrodes comprise a conductive sponge comprising a two-part silicone foam, a silicone thinning fluid, and carbon fiber, and a sponge seat comprising a silicone or thermoplastic elastomer material, wherein the conductive sponge is disposed within the sponge seat; and one or more wires printedly embedded in the head covering that connect the one or more electrodes to external electronics.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which:

FIG. 8 illustrates an embodiment of one or more electrode-connecting wires according to embodiments of the present invention;

FIG. 9 illustrates an embodiment of one or more electrode-connecting wires according to embodiments of the present invention; and FIG. 10 illustrates a computer board according to embodiments of the present invention.

DETAILED DESCRIPTION OF THE PREFERRED EMBODIMENTS

Figure 1:
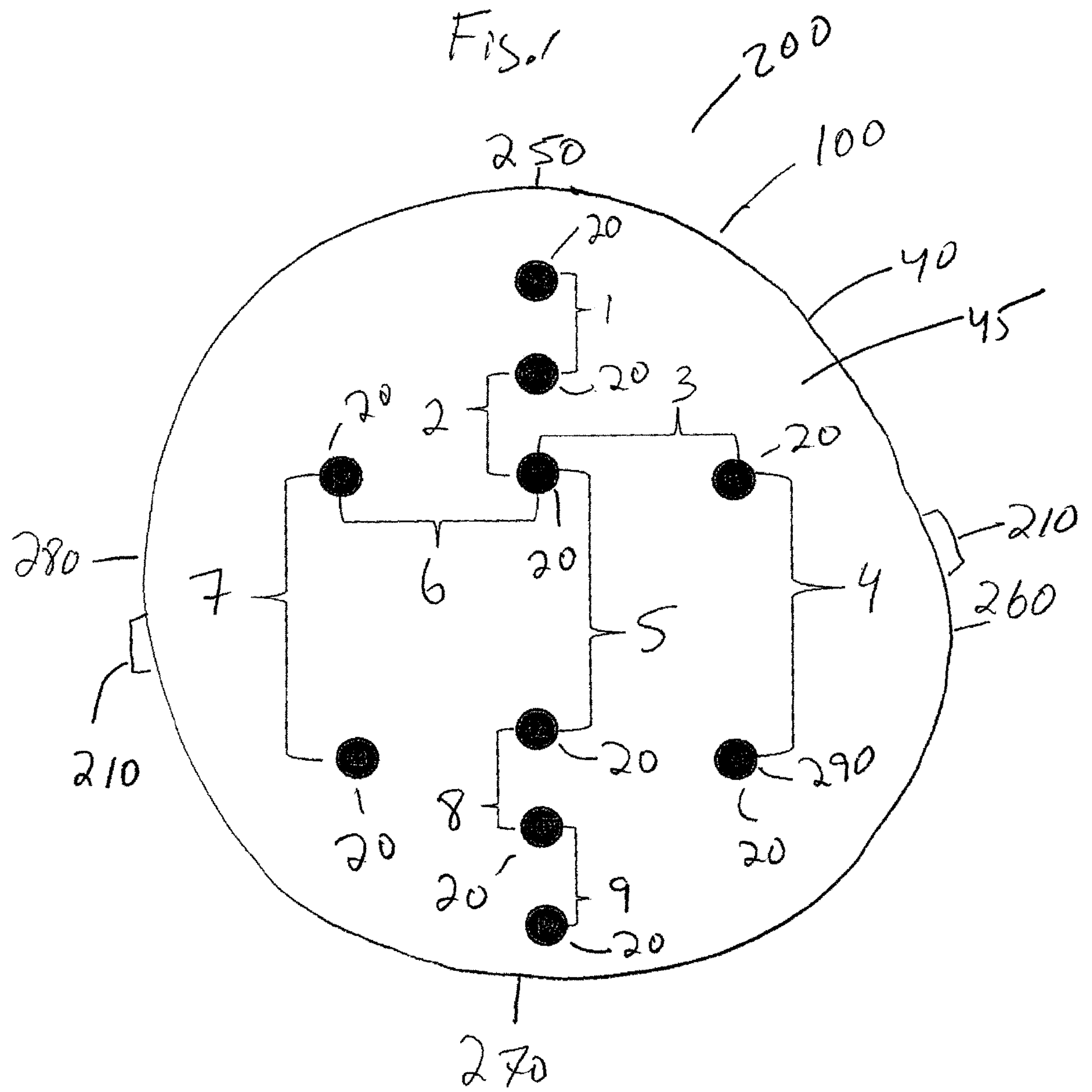
FIG. 1 illustrates a mapping of electrodes for an EEG cap according to embodiments of the present invention.

In embodiments as shown in FIG. 1, the present invention relates to an improved, universally fitting EEG cap 200 for use with new or existing EEG systems that non-invasively measure a brain's electrical activity via electrodes, connecting wires, amplifiers, a computer control module, and a display device. In embodiments, the improved, universally fitting EEG cap 200 may comprise a head covering 100, one or more electrodes 20, and one or more electrode-connecting wires 400.

In embodiments as shown in FIG. 1, EEG cap 200 includes head covering 100. Head covering 100 may be at least one layer of an elastic fabric manufactured and configured in such a way as to fit over and conform to a user's head. In embodiments, the elastic fabric may comprise an auxetic material that when stretched, stressed, loaded, or placed under a tension force, becomes thicker and stronger, contrary to other elastic fabrics. Any suitable auxetic material may be used. By nature of this auxetic material, the head covering of the EEG cap 200 may be capable of fitting over and conforming to the heads of various users, regardless of head shape or size, and may do so without compromising on strength, durability, and comfort. In further embodiments, the elastic fabric may comprise the auxetic material and one or more additional fabric materials such as, without limitation, cotton, nylon, or combinations thereof. In such embodiments, the auxetic material or auxetic fibers may be woven into the fibers of the one or more additional fabric materials to create a special fabric blend for the head covering. An auxetic material utilized by the present invention may be described in U.S. Pat. Nos. 8,916,262 and 9,962,313, the disclosures of which are incorporated by reference herein in their entirety. In some embodiments as shown in FIG. 1, head covering 100 may comprise two fabric layers, inner layer 45 and outer layer 40. The first or inner layer 45 (i.e., the layer closest to the user's head) may be any suitable fabric for disposition against the user's head. In some embodiments, inner layer 45 is an active cooling fabric that aids in keeping the user cool during operation. Without limitation, embodiments of inner layer 45 comprise cotton, linen, nylon, polyester, rayon, silk, wool, or any combinations thereof. In some embodiments, inner layer 45 comprises cotton, linen, nylon, polyester, rayon, silk, wool, auxetic materials, or any combinations thereof. The second or outer layer 40, (i.e., the layer furthest from the user's head) may be a fabric of auxetic fibers. In embodiments, outer layer 40 includes auxetic fibers weaved into other fibers. Any suitable other fibers may be used such as cotton, nylon, or combinations thereof. In further embodiments, the head covering 100 may further comprise a fastening mechanism 210 to aid in securing the head covering 100 to a user's head. In an embodiment, outer layer 40 provides compression to the top of electrodes 20 which presses downward providing a sufficient contact with the scalp of the user. In embodiments, at least one or all of electrodes 20 are disposed between outer layer 40 and inner layer 45. In an embodiment, electrodes 20 protrude through inner layer 45 providing contact with the scalp of the user. In embodiments as shown, electrodes 20 protrude through holes 290 in inner layer 45. Holes 290 may be provided by any suitable method such as by die cut of holes 290 in inner layer 45. In embodiments, fastening mechanism 210 may include any suitable mechanism for securing head covering 100 to a user's head. In embodiments, fastening mechanism 210 is a strap, buckle, or combination thereof. The fastening strap or buckle may be any fastening strap or buckle known to one of ordinary skill in the art that may be attached to head covering 100 in a configuration that allows the fastening strap or buckle to be secured to the user such as under the user's chin.

The one or more electrodes 20 may be disposed on an inner surface of the head covering 100 whereby the one or more electrodes 20 may be in contact with the user's head during operation. In embodiments as shown in FIG. 1, electrodes 20 are disposed on inner layer 45. Head covering 100 may include any suitable number of electrodes 20. In embodiments, the one or more electrodes 20 may be placed at or mapped to any suitable location on the head covering 100. In one particular embodiment, the electrodes 20 may be placed on the head covering 100 according to EEG montage 500 shown in FIG. 1, which graphically illustrates a particular mapping of electrodes for the EEG cap 200. In such embodiments, EEG cap 200 has, in relation to placement on a user's head, front of cap 250, right of cap 260, back of cap 270, and left of cap 280. In such EEG montage 500, embodiments include EEG montage 500 comprising FpZ electrode 20, GND electrode 20, FZ electrode 20, F4 electrode 20, C4 electrode 20, Cz electrode 20, REF electrode 20, Pz electrode 20, F3 electrode 20, and C3 electrode 20. FpZ electrode 20 and GND electrode 20 may have any suitable center to center measurement 1, such as between about 25 mm and about 40 mm, alternatively at about 32 mm. GND electrode 20 and FZ electrode 20 may have any suitable center to center measurement 2, such as between about 25 mm and about 45 mm, alternatively at about 36 mm. FZ electrode 20 and F4 electrode 20 may have any suitable center to center measurement 3, such as between about 40 mm and about 60 mm, alternatively at about 47 mm. F4 electrode 20 and C4 electrode 20 may have any suitable center to center measurement 4, such as between about 50 mm and about 70 mm, alternatively at about 61 mm. FZ electrode 20 and Cz electrode 20 may have any suitable center to center measurement 5, such as between about 55 mm and about 80 mm, alternatively at about 67 mm. FZ electrode 20 and F3 electrode 20 may have any suitable center to center measurement 6, such as between about 40 mm and about 55 mm, alternatively at about 47 mm. F3 electrode 20 and C3 electrode 20 may have any suitable center to center measurement 7, such as between about 50 mm and about 70 mm, alternatively at about 61 mm. CZ electrode 20 and REF electrode 20 may have any suitable center to center measurement 8, such as between about 30 mm and about 40 mm, alternatively at about 35 mm. REF electrode 20 and Pz electrode 20 may have any suitable center to center measurement 9, such as between about 30 mm and about 40 mm, alternatively at about 35 mm. In embodiments of such EEG montage 500, F3 electrode 20 is disposed on left of cap 280 opposing F4 electrode 20 disposed on right of cap 260, C3 electrode 20 is on left of cap 280 opposing C4 electrode 20 disposed on right of cap 260. Further in embodiments of EEG montage 500, FpZ electrode 20 is disposed on front of cap 250 opposing Pz electrode 20 disposed on back of cap 270, GND electrode 20 is disposed on front of cap 250 opposing REF electrode 20 disposed on back of cap 270, with GND electrode 20 disposed between FpZ electrode 20 and FZ electrode 20 and with REF electrode 20 disposed between Cz electrode 20 and Pz electrode 20. Additionally in embodiments, FZ electrode 20 is disposed between F3 electrode 20 and F4 electrode 20, and Cz electrode 20 is disposed between C3 electrode 20 and C4 electrode 20. In embodiments, a tail of at least one of the electrodes 20 exits head covering 100 at back of cap 270. It is to be understood that EEG cap 200 may include any other suitable EEG montage and is not limited to EEG montage 500.

Figure 2:
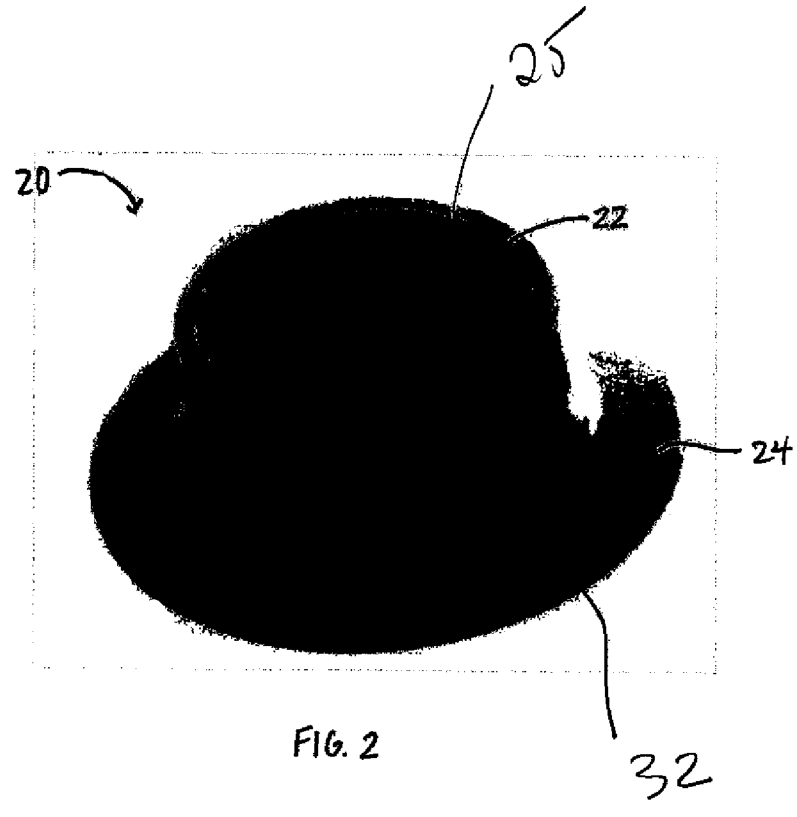
FIG. 2 illustrates an electrode according to embodiments of the present invention.

Regardless of placement, each of the one or more electrodes 20 may comprise a conductive sponge 22 and a sponge seat 24, as illustrated in FIG. 2. Conductive sponge 22 may comprise any suitable conductive sponge material. In embodiments, conductive sponge 22 includes a two-part silicone foam, a silicone thinning fluid, carbon fiber, or any combinations thereof. In embodiments, part A of the two-part silicone foam may be present in an amount between about 0.01 g and about 10.0 g, or alternatively between about 1.0 g and about 7.5 g, or further alternatively between about 2.0 g and about 5.0 g. In an embodiment, part A is a silicone foam. Part B of the two-part silicone foam may be present in an amount between about 0.01 g and about 10.0 g, or alternatively between about 0.1 g and about 5.0 g, or further alternatively between about 1.0 g and about 3.0 g. In an embodiment, part B is a curing agent. The silicone thinning fluid may be present in an amount between about 0.01 g and about 5.0 g, or alternatively between about 0.1 g and about 1.0 g. The carbon fiber may be present in amount between about 0.01 g and about 5.0 g, or alternatively between about 0.1 g and about 1.0 g. A conductive sponge utilized by the present invention may be described in International Application Publication No. WO 2020/010219 A9, the disclosure of which is incorporated by reference herein in its entirety.

This configuration of conductive sponge 22 may facilitate the conductivity of the one or more electrodes 20. During operation, each conductive sponge 22 may be dry or alternatively saturated with water, saline, or the like. For instance, conductive sponge 22 may be wetted with a 0.9% saline solution and inserted into sponge seat 24. In embodiments, an electrode 20 with a dry conductive sponge 22 may achieve an impedance comparable to that of a standard dry electrode known to one of ordinary skill in the art. However, an electrode 20 with a wet conductive sponge 20 may achieve an impedance of about 2 kΩ at 1 KHz, which may be lower than a standard wet gold cup electrode with electrode gel and a standard disposable hydrogel electrode.

Figure 7:
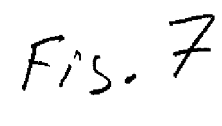
FIG. 7 illustrates an embodiment of section B of the electrode embodiment of FIG. 6.
Figure 7:
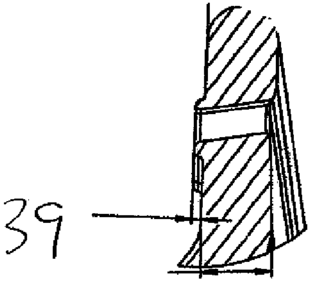
Figure 3:
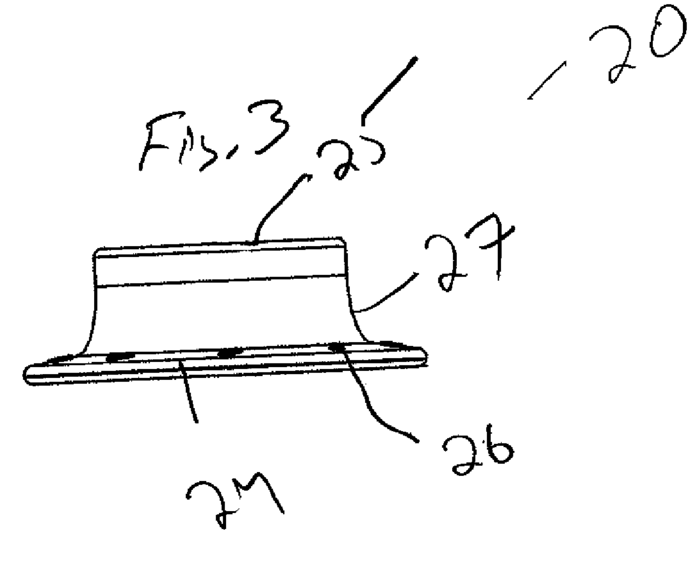
FIG. 3 illustrates an electrode according to embodiments of the present invention.
Figure 4:
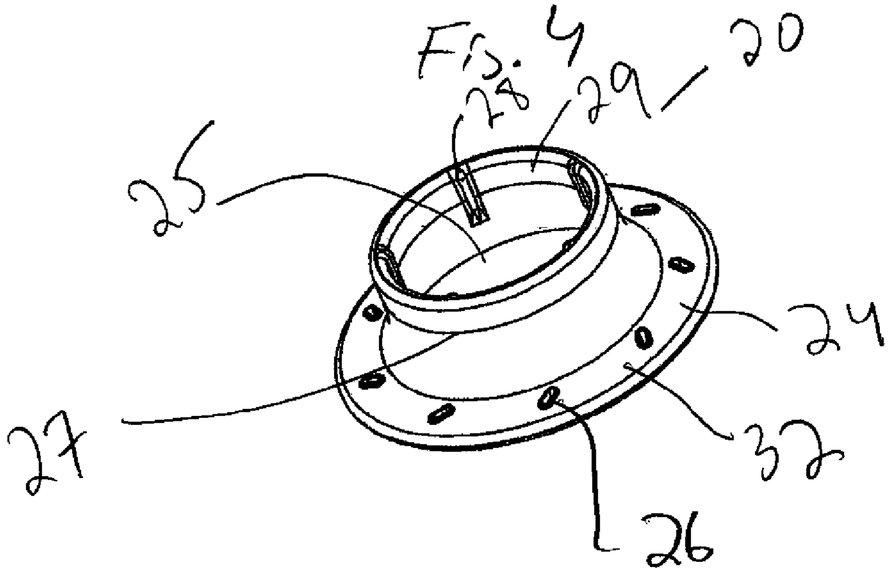
FIG. 4 illustrates a perspective view of an electrode according to embodiments of the present invention.
Figure 6:
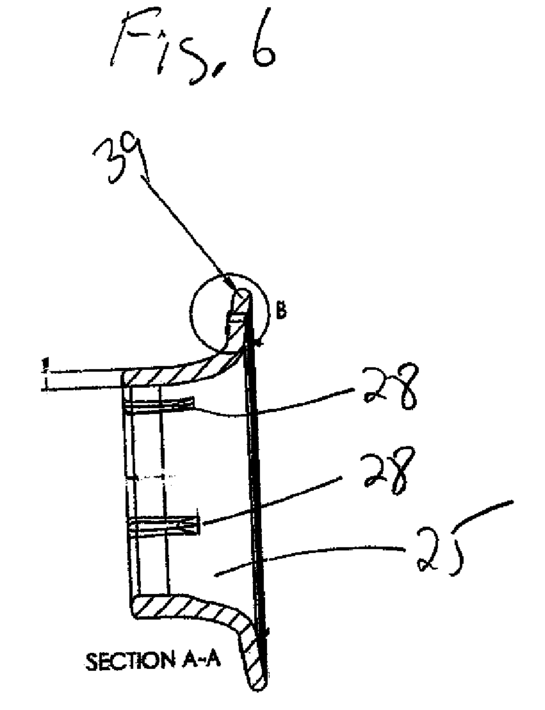
FIG. 6 illustrates an embodiment of the electrode of FIG. 5 of cross section A-A.

Sponge seat 24 may be for housing conductive sponge 22. Sponge seat 24 may have any suitable configuration for use with EEG cap 200. In embodiments as shown in FIG. 2, sponge seat 24 may have sponge holder 27 of a substantially cylindrical configuration comprising an internal bore 25. Sponge seat 24 may also have flange 32. Flange 32 may have any suitable configuration. In embodiments, flange 32 has a substantially flat underside. Flange 32 may also have securing means 26. Securing means 26 may be disposed in any configuration suitable for facilitating securing of sponge seat 24. In embodiments, securing means 26 may be radially distributed about flange 32 in an off-set configuration as illustrated. As shown in FIGS. 6 and 7, securing means 36 comprise sewing loops 39. Sewing loops 39 are suitable for securing electrode 20 to fabric such as head covering 100.

In embodiments, sponge seat 24 may comprise any suitable material such as, without limitation, silicone, a thermoplastic elastomer (TPE) material, or any combinations thereof. These materials may be conductive as well as increase comfort for the user during operation. In embodiments, the dimensions of sponge seat 24 may be any suitable dimensions, with internal bore 25 corresponding with the dimensions of conductive sponge 22, such that conductive sponge 22 may be securely disposed or seated within the internal bore 25 of sponge seat 24 by any suitable means. FIGS. 2, 3, 4, 5, 6 and 7 illustrate a particular embodiment of sponge seat 24. Sponge 22 is disposed in internal bore 25. Raised edges 28 are disposed on walls 29 of internal bore 25. Raised edges 28 are disposed radially about internal bore 25. Without limitation, raised edges 28 facilitate securing of conductive sponge 22 in internal bore 25.

In embodiments as shown, one or more electrodes 20, comprising conductive sponge 22 and sponge seat 24, may be attached to the head covering 100 by any suitable means, whereby the auxetic characteristics of the head covering fabric 100 facilitating attachment. In some embodiments, and particularly those in which the head covering 100 comprises two fabric layers (i.e., outer layer 40 and inner layer 45), one or more electrodes 20 may be disposed within die cutouts made on the inner layer 45 of the head covering 100. This may allow one or more electrodes 20 to be secured between the inner layer 45 and outer layer 40 of the head covering 100 as well as protrude through the inner layer 45 to make contact with the user's head during operation. In such embodiments, the outer layer 40 of the head covering 100 may provide compression to the top of each of the one or more electrodes 20. By this compression, the head covering 100 may ensure that each of the one or more electrodes 20 have adequate contact with the user's head as well as elicit an automated function of pressing each the of one or more electrodes 20 into place.

As shown in FIGS. 8 and 9, EEG cap 200 may include one or more electrode-connecting wires 400 embedded in head covering 100 which are capable of connecting one or more electrodes 20 to any EEG electronics. In embodiments, the one or more electrode-connecting wires 400 may be conductive wires 405 printed on a thin substrate 410 that may be heat transferred to textiles such as the fabric of head covering 100 via any suitable means such as via equipment known to one of ordinary skill in the art in the garment decorating industry. In embodiments, thin substrate 410 is attached to head covering 100. In some embodiments, thin substrate 410 is attached to inner layer 45. The ink used to print the one or more electrode-connecting wires 400 onto the thin substrate 410, as well as the thin substrate 410 itself, may have the ability to stretch and flex with the fabric of head covering 100 once effectively applied. In some embodiments, and particularly those in which head covering 100 comprises two fabric layers (i.e., outer layer 40 and inner layer 45), the one or more electrode-connecting wires 400 may be disposed between inner layer 45 and outer layer 40. In embodiments, thin substrate 410 is attached to head covering 100. In some embodiments, thin substrate 410 is attached to inner layer 45. FIGS. 8 and 9 illustrate one embodiment of the one or more electrode-connecting wires 400. In this particular embodiment, the one or more electrode-connecting wires 400 may be split into two circuits corresponding to various electrodes 20, however the one or more electrode-connecting wires 400 may be split into any number of circuits, or alternatively comprise only one circuit.

Figure 5:
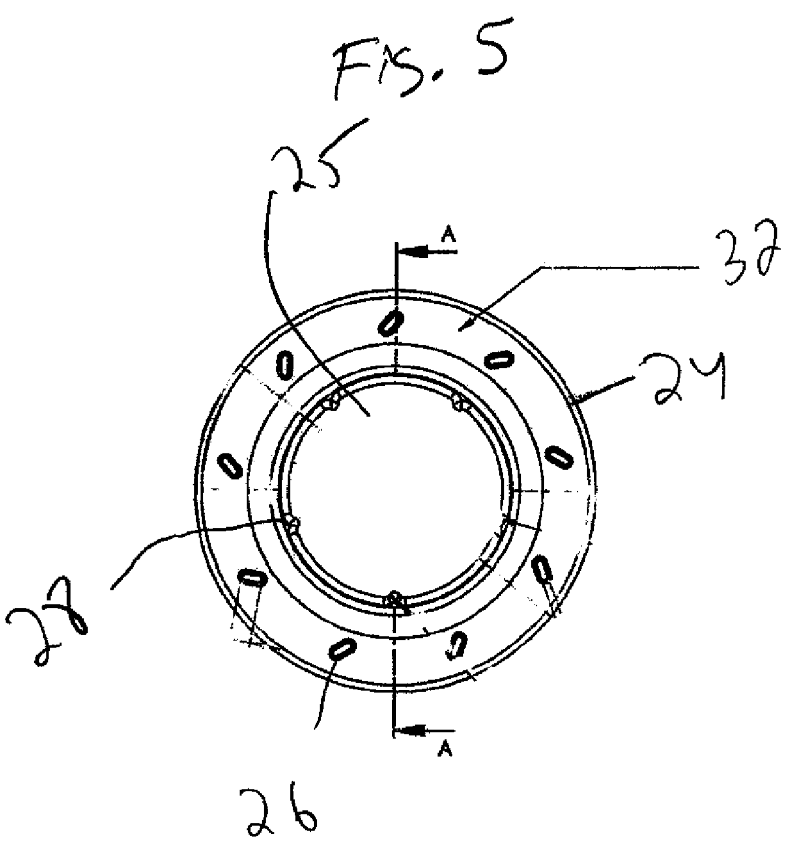
FIG. 5 illustrates an embodiment of the electrode according to embodiments of the invention.

In embodiments, the one or more electrode-connecting wires 400 may be connected to any EEG electronics used to monitor and/or record activity measured by the one or more electrodes 20. EEG electronics may comprise, without limitation a computer board 600 that will process any measured EEG data. In embodiments, the computer board may comprise an A/D convertor, EEG software, BLE transmitters, and an accelerometer. Further, the EEG software used to process said EEG data may be an open-source product. In some embodiments, the computer board may comprise Bluetooth capabilities that allow for wireless connection to an external device, such as a cell phone, smart phone, computer, or the like. FIG. 5 illustrates one embodiment of computer board 600.

Although the present invention and its advantages have been described in detail, it should be understood that various changes, substitutions and alterations may be made herein without departing from the spirit and scope of the invention as defined by the appended claims.

What is claimed is:

1. An electroencephalogram (EEG) cap, comprising:

a head covering comprising auxetic material, wherein the auxetic material allows the head covering configured to be disposed upon and conform to a head, and wherein the head covering comprises an inner layer and an outer layer;

one or more electrodes, wherein the one or more electrodes are disposed on the inner layer, wherein each of the one or more electrodes comprise:

a conductive sponge comprising a two-part silicone foam, a silicone thinning fluid, carbon fiber, or any combinations thereof; and a sponge seat comprising a silicone or thermoplastic elastomer material, wherein the conductive sponge is securely disposed within the sponge seat; and one or more electrode-connecting wires printedly embedded in the head covering that connect the one or more electrodes to external electronics;

wherein the electrode-connecting wires are split into two circuits corresponding to particular electrodes of the one or more electrodes.

2. The electroencephalogram (EEG) cap of claim 1, wherein the one or more electrodes protrude through the inner layer.

3. The electroencephalogram (EEG) cap of claim 1, further comprising a fastening mechanism for securing the head covering to the head.

4. The electroencephalogram (EEG) cap of claim 1, wherein the outer layer comprises compression to a top of the one or more electrodes.

5. The electroencephalogram (EEG) cap of claim 1, further comprising an EEG cap montage consisting of FpZ, GND, FZ, F3, F4, Cz, C3, C4, REF, and Pz.

6. The electroencephalogram (EEG) cap of claim 1, wherein each electrode of the one or more electrodes comprises a conductive sponge and a sponge seat.

7. The electroencephalogram (EEG) cap of claim 6, wherein the sponge comprises a two-part silicone foam, a silicone thinning fluid, and a carbon fiber.

8. The electroencephalogram (EEG) cap of claim 7, wherein the two-part silicone foam comprises a part A, wherein the part A is present in an amount between 0.01 g and 10.0 g.

9. The electroencephalogram (EEG) cap of claim 8, wherein the part A comprises a silicone foam.

10. The electroencephalogram (EEG) cap of claim 7, wherein the two-part silicone foam comprises a part B, wherein the part B is present in an amount between 0.01 g and 10.0 g.

11. The electroencephalogram (EEG) cap of claim 10, wherein the part B comprises a curing agent.

12. The electroencephalogram (EEG) cap of claim 7, wherein the silicone thinning fluid is present in an amount between 0.01 g and 5.0 g.

13. The electroencephalogram (EEG) cap of claim 7, wherein the carbon fiber is present in an amount between 0.01 g and 5.0 g.

14. The electroencephalogram (EEG) cap of claim 6, wherein the sponge is securely disposed in the sponge seat.

15. The electroencephalogram (EEG) cap of claim 14, wherein the sponge seat comprises a sponge holder of a cylindrical configuration comprising an internal bore, wherein the sponge is disposed in the internal bore.

16. The electroencephalogram (EEG) cap of claim 15, wherein the internal bore comprises raised edges disposed on a wall of the internal bore, wherein the raised edges are disposed radially about the internal bore.

17. The electroencephalogram (EEG) cap of claim 6, wherein the sponge seat comprises a flange.

18. The electroencephalogram (EEG) cap of claim 17, wherein the flange comprises securing means.

19. The electroencephalogram (EEG) cap of claim 6, wherein the sponge seat of each electrode comprises silicone, a thermoplastic elastomer, or any combinations thereof.

20. An electroencephalogram (EEG) cap, comprising:

a head covering comprising auxetic material, wherein the auxetic material allows the head covering configured to be disposed upon and conform to a head, and wherein the head covering comprises an inner layer and an outer layer;

one or more electrodes, wherein the one or more electrodes are disposed in between the inner layer and the outer layer, wherein each of the one or more electrodes comprise:

a conductive sponge comprising a two-part silicone foam, a silicone thinning fluid, carbon fiber, or any combinations thereof; and a sponge seat comprising a silicone or thermoplastic elastomer material, wherein the conductive sponge is securely disposed within the sponge seat; and one or more electrode-connecting wires printedly embedded in the head covering that connect the one or more electrodes to external electronics;

wherein:

each electrode of the one or more electrodes comprises a conductive sponge and a sponge seat;

the sponge comprises a two-part silicone foam, a silicone thinning fluid, a carbon fiber, or any combinations thereof; and the two-part silicone foam comprises a part A, wherein the part A is present in an amount between 0.01 g and 10.0 g.

21. The electroencephalogram (EEG) cap of claim 20, wherein the part A comprises a silicone foam.

22. An electroencephalogram (EEG) cap, comprising:

a head covering comprising auxetic material, wherein the auxetic material allows the head covering configured to be disposed upon and conform to a head, and wherein the head covering comprises an inner layer and an outer layer;

one or more electrodes, wherein the one or more electrodes are disposed in between the inner layer and the outer layer, wherein the outer layer compresses each of the one or more electrodes to contact the scalp of the user, wherein each of the one or more electrodes comprise:

a conductive sponge comprising a two-part silicone foam, a silicone thinning fluid, carbon fiber, or any combinations thereof; and a sponge seat comprising a silicone or thermoplastic elastomer material, wherein the conductive sponge is securely disposed within the sponge seat; and one or more electrode-connecting wires printedly embedded in the head covering that connect the one or more electrodes to external electronics;

wherein:

each electrode of the one or more electrodes comprises a conductive sponge and a sponge seat;

the sponge comprises a two-part silicone foam, a silicone thinning fluid, a carbon fiber, or any combinations thereof; and the two-part silicone foam comprises a part B, wherein the part B is present in an amount between 0.01 g and 10.0 g.

23. The electroencephalogram (EEG) cap of claim 22, wherein the part B comprises a curing agent.

24. An electroencephalogram (EEG) cap, comprising:

a head covering comprising auxetic material, wherein the auxetic material allows the head covering configured to be disposed upon and conform to a head, and wherein the head covering comprises an inner layer and an outer layer;

one or more electrodes, wherein the one or more electrodes are disposed in between the inner layer and the outer layer and protrude through the inner layer, wherein each of the one or more electrodes comprise:

a conductive sponge comprising a two-part silicone foam, a silicone thinning fluid, carbon fiber, or any combinations thereof; and a sponge seat comprising a silicone or thermoplastic elastomer material, wherein the conductive sponge is securely disposed within the sponge seat; and one or more electrode-connecting wires printedly embedded in the head covering that connect the one or more electrodes to external electronics;

wherein:

each electrode of the one or more electrodes comprises a conductive sponge and a sponge seat;

the sponge comprises a two-part silicone foam, a silicone thinning fluid, a carbon fiber, or any combinations thereof; and the silicone thinning fluid is present in an amount between 0.01 g and 5.0 g.

25. An electroencephalogram (EEG) cap, comprising:

a head covering comprising auxetic material, wherein the auxetic material allows the head covering configured to be disposed upon and conform to a head, and wherein the head covering comprises an inner layer and an outer layer;

one or more electrodes, wherein the one or more electrodes are disposed in between the inner layer and the outer layer, wherein each of the one or more electrodes comprise:

a conductive sponge comprising a two-part silicone foam, a silicone thinning fluid, carbon fiber, or any combinations thereof; and a sponge seat comprising a silicone or thermoplastic elastomer material, wherein the conductive sponge is securely disposed within the sponge seat; and one or more electrode-connecting wires printedly embedded in the head covering that connect the one or more electrodes to external electronics;

wherein:

each electrode of the one or more electrodes comprises a conductive sponge and a sponge seat;

the sponge seat comprises a sponge holder of a cylindrical configuration comprising an internal bore comprises one or more raised edges disposed radially about the wall of the internal bore, wherein the sponge is disposed in the internal bore and secured by the raised edges of the internal bore;

the sponge comprises a two-part silicone foam, a silicone thinning fluid, a carbon fiber, or any combinations thereof; and the carbon fiber is present in an amount between 0.01 g and 5.0 g.

26. An electroencephalogram (EEG) cap, comprising:

a head covering comprising auxetic material, wherein the auxetic material allows the head covering configured to be disposed upon and conform to a head, and wherein the head covering comprises an inner layer and an outer layer;

one or more electrodes, wherein the one or more electrodes are disposed on the inner layer, wherein each of the one or more electrodes comprise:

a conductive sponge comprising a two-part silicone foam, a silicone thinning fluid, carbon fiber, or any combinations thereof; and a sponge seat comprising a silicone or thermoplastic elastomer material, wherein the conductive sponge is disposed within the sponge seat; and one or more electrode-connecting wires printedly embedded in the head covering that connect the one or more electrodes to external electronics wherein:

each electrode of the one or more electrodes comprises a conductive sponge and a sponge seat;

the conductive sponge is securely disposed within the sponge seat; and the sponge seat comprises a sponge holder of a cylindrical configuration comprising an internal bore comprises one or more raised edges disposed radially about the internal bore, wherein the sponge is disposed in the internal bore and secured by the raised edges of the internal bore.

27. An electroencephalogram (EEG) cap, comprising:

a head covering comprising auxetic material, wherein the auxetic material allows the head covering configured to be disposed upon and conform to a head, and wherein the head covering comprises an inner layer and an outer layer;

one or more electrodes, wherein the one or more electrodes are disposed on the inner layer, wherein each of the one or more electrodes comprise:

a conductive sponge comprising a two-part silicone foam, a silicone thinning fluid, carbon fiber, or any combinations thereof; and a sponge seat comprising a silicone or thermoplastic elastomer material, wherein the conductive sponge is securely disposed within the sponge seat; and one or more electrode-connecting wires printedly embedded in the head covering that connect the one or more electrodes to external electronics;

wherein:

each electrode of the one or more electrodes comprises a conductive sponge and a sponge seat;

the sponge seat comprises a sponge holder of a cylindrical configuration comprising an internal bore comprises one or more raised edges disposed on the wall of the internal bore, wherein the sponge is disposed in the internal bore and secured by the raised edges of the internal bore;

the sponge seat comprises a flange; and the flange comprises securing means.

* * * * *